(12) United States Patent
Liu et al.

(10) Patent No.: US 8,126,108 B2
(45) Date of Patent: Feb. 28, 2012

(54) METHOD AND APPARATUS FOR REORIENTATED RESCONSTRUCTION OF COMPUTED TOMOGRAPHY IMAGES OF PLANAR OBJECTS

(75) Inventors: Tong Liu, Singapore (SG); Andrew A. Malcolm, Singapore (SG); Jian Xu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/596,661

(22) PCT Filed: Apr. 18, 2007

(86) PCT No.: PCT/SG2007/000104
§ 371 (c)(1),
(2), (4) Date: Sep. 23, 2010

(87) PCT Pub. No.: WO2008/130325
PCT Pub. Date: Oct. 30, 2008

(65) Prior Publication Data
US 2011/0007864 A1    Jan. 13, 2011

(51) Int. Cl.
A61B 6/00 (2006.01)
(52) U.S. Cl. .................. 378/4; 378/21; 382/131
(58) Field of Classification Search .......... 378/4, 19; 382/131
See application file for complete search history.

(56) References Cited

U.S. PATENT DOCUMENTS

| | | | |
|---|---|---|---|
| 4,888,693 A | 12/1989 | Tam | |
| 6,898,266 B2 * | 5/2005 | Griffith | 378/22 |
| 6,996,265 B1 * | 2/2006 | Patnaik | 382/149 |
| 7,496,222 B2 * | 2/2009 | Mussack et al. | 382/131 |
| 7,978,191 B2 * | 7/2011 | Liao | 345/419 |
| 2005/0047637 A1 | 3/2005 | Greenbaum et al. | |
| 2006/0153434 A1 * | 7/2006 | Wang | 382/128 |
| 2007/0003002 A1 | 1/2007 | Chen et al. | |
| 2007/0009079 A1 | 1/2007 | Chen et al. | |

FOREIGN PATENT DOCUMENTS

| | | |
|---|---|---|
| GB | 2192120 A | 12/1987 |
| WO | WO 2007/043974 A1 | 4/2007 |

* cited by examiner

*Primary Examiner* — Alexander H Taningco
(74) *Attorney, Agent, or Firm* — Knobbe Martens Olson & Bear LLP (57) ABSTRACT

A system and method for micro computed tomography (CT) reconstruction of position scan data of planar objects, such as stacked integrated circuit chips and/or PCB, that automatically determines object orientation is disclosed for a preferred orientation of the reconstructed images. The object orientation of the sinogram of the scanning data is determined such that the reconstruction may be performed with any starting position. Additionally, planar object scan reconstructions with either a higher resolution in the thickness dimension without increasing the total computation resource or a faster processing speed under a given resolution in the thickness dimension may be achieved. The tilting angle with respect to the rotation axis may also be determined to perform a image rotation after a multi-slice reconstruction or cone-beam reconstruction.

34 Claims, 13 Drawing Sheets

METHOD AND APPARATUS FOR REORIENTATED RESCONSTRUCTION OF COMPUTED TOMOGRAPHY IMAGES OF PLANAR OBJECTS

RELATED APPLICATIONS

This application is a U.S. National Phase of International Application No.: PCT/SG2007/000104, filed Apr. 18, 2007, designating the U.S. and published in English on Oct. 30, 2008 as WO 2008/130325.

FIELD OF THE INVENTION

This invention relates to reconstruction of computed tomography (CT) scanning data, and more particularly, determination of object orientation from the scanning data for reconstruction with a preferred orientation.

BACKGROUND OF THE INVENTION

Micro CT is widely used in many applications, for example, for hidden defect inspection in semiconductor, electronics, advanced material and bioscience industries. One increasingly important category of the applications is the internal layer separation and inspection of planar multi-layered electronics as advanced packaging technologies are becoming dominant in the manufacturing process. To obtain the pattern of each individual layer and to check the quality of the corresponding manufacturing process, it is a general requirement from users to non-destructively separate the individual layers parallel to the primary plane of the object.

Figure 1A:
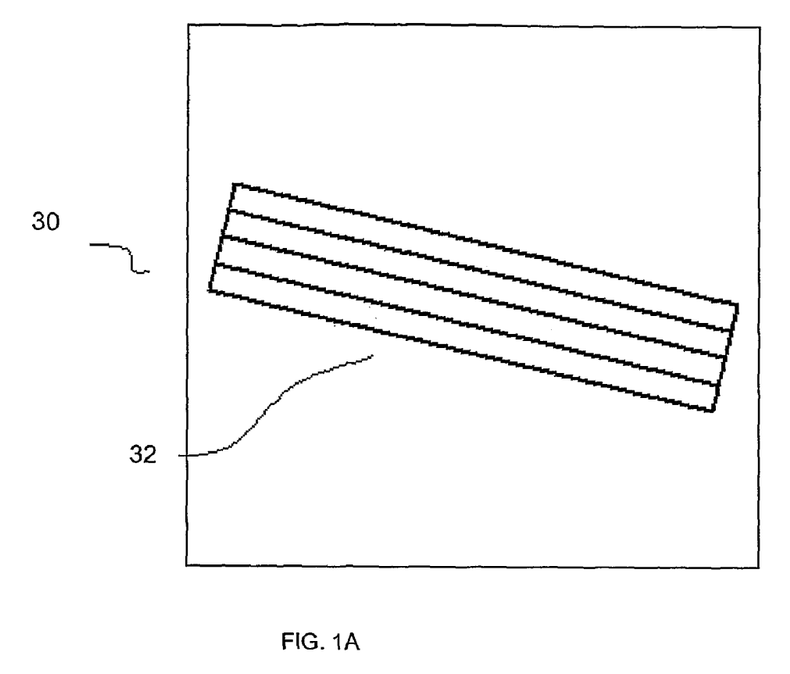
FIG. 1A-E are general reconstruction images (FIG. 1A-D) and re-reconstruction image (FIG. 1E) of CT scan data rendered from conventional systems and methods in the prior art.
Figure 1B:
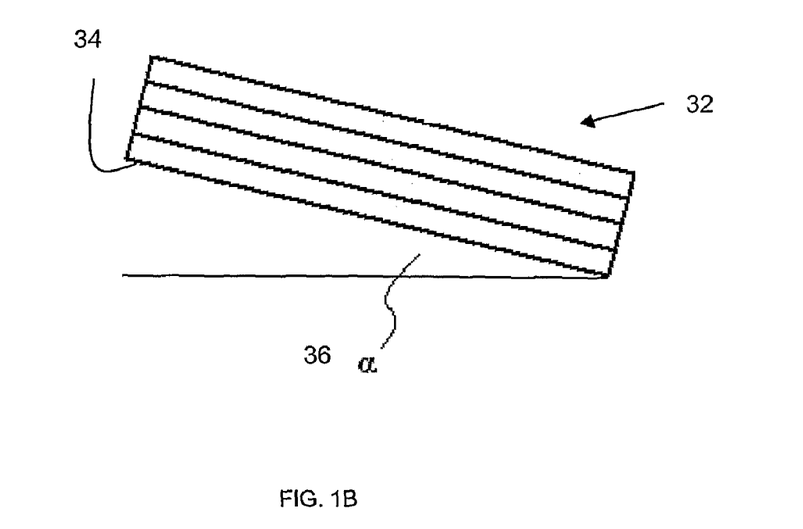

There are several current common approaches. FIG. 1A illustrates a general reconstructed CT image or reconstruction matrix 30. A first approach typically taken is shown in FIG. 1B to reconstruct one slice first, with which one manually measures the slant angle 36 of the reconstructed image 30, and restarts the reconstruction process for all slices with that angle identified 36 of the reconstructed object 30. The slant angle 36 of the object 30 is measured in a conventional system by picking two points along the edge 34 and applying a triangular function. Then the measured angle is used in a re-reconstruction process as the starting angle which leads to the edges of the reconstructed image aligned with the dimensions of the reference plane and reconstruction matrix to render the orientated reconstructed image ore reconstructed slices of a multi layered planar object 32 shown in FIG. 1E.

Figure 1C:
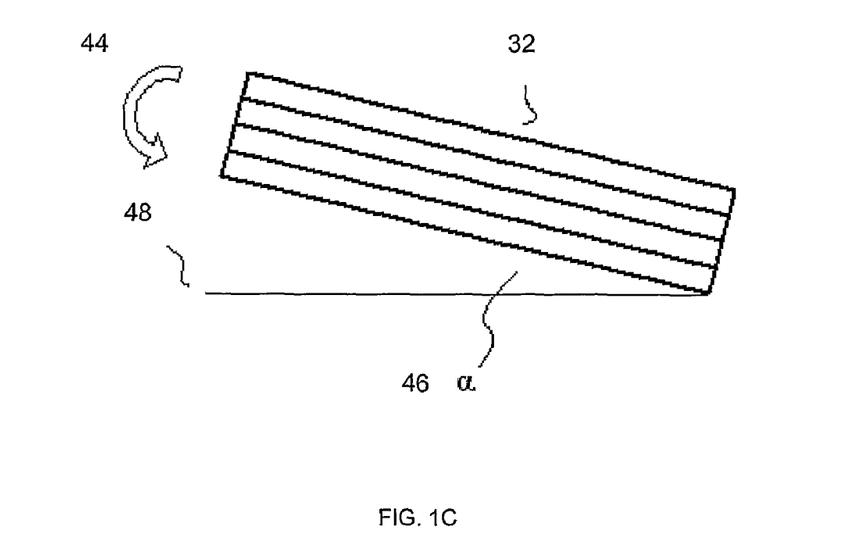
Figure 1D:
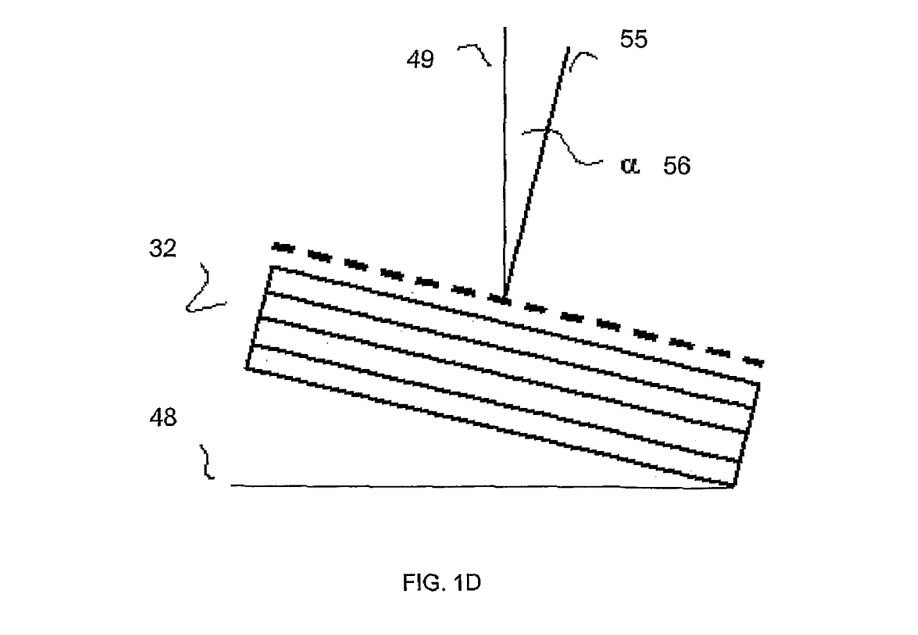
Figure 1E:
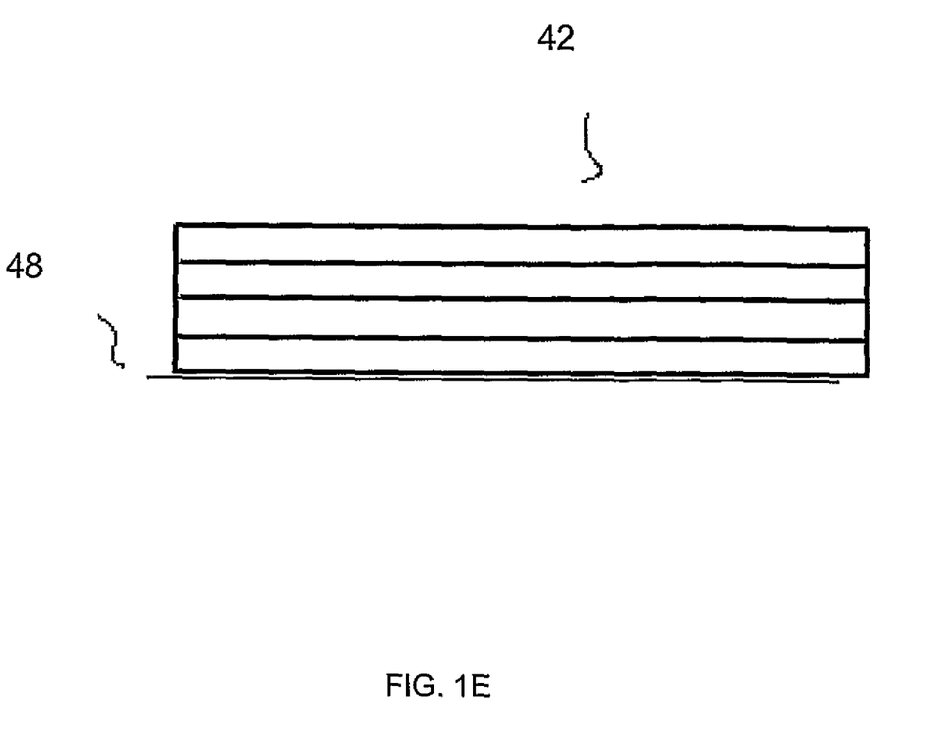

In another approach the slant angle 46 of the reconstructed image 30 is also calculated, as shown in FIG. 1C, however, instead of re-reconstructing the CT slices as shown in the system shown in FIG. 1B, an image rotation 44 is performed of the angle identified 46 relative to a reference plane/reconstruction matrix dimension 48 of all the reconstructed images 32 to achieve the preferred orientated reconstructed image 42 shown in FIG. 1E.

In another approach, shown in FIG. 1D, the primary plane of the reconstructed object is carefully identified and then defined as the clipping plane so that the internal layers can be displayed properly. The object projection is cut along the direction defined by the cut-plane (or clip-plane) 54. The cut-plane is defined carefully to match with a cut-plane angle 56(α) as accurate as possible the orientation of the object which is generally a time-consuming process requiring skilled operators. The cut plane angle is defined as the angle formed between the normal of the cutting plane 55 and the normal of the reference plane or reconstruction matrix dimension 49.

All the above mentioned conventional methods need to manually determine the object orientation after the reconstruction for at least one slice and then perform image rotations or redo the reconstruction. This not only slows down the image processing and adds additional computing resource, but also makes the layer separation and interpretation work only accessible to well-trained users.

There is a need for CT reconstruction method for planar objects with automatically determined orientation that addresses at least one of the above limitations in the prior art.

SUMMARY OF THE INVENTION

In accordance with an aspect of the invention a method is provided for reconstruction of computed tomography (CT) scanning data of an object, comprising receiving CT scanning data of at least one slice of a scanned object; identifying specific object orientation data representative of a physical feature of the object in a slice of the CT scanning data; corresponding the identified specific object orientation data with the identified projection angle associated with the orientation data to determine the identified orientation of the object; reconstructing the CT scanning data into reconstructed data in accordance with the identified object orientation data, identified projection angle and the identified orientation, the reconstructed data capable to be rendered to create a visual expression representative of the object having a predetermined orientation regardless of the starting position of the CT scanning position.

An embodiment of the invention is a method for determining the object orientation with the sinogram of the scanning, with which the reconstruction may be performed with any starting position, giving the preferred orientation to the reconstructed images. An embodiment of the invention reconstructs a planar object with either a higher resolution in the thickness dimension without increasing the total computation resource or a faster processing speed under a given resolution in the thickness dimension. An embodiment of the invention determines the tilting angle with respect to the rotation axis and perform a image rotation after a multi-slice reconstruction or cone-beam reconstruction.

An aspect of the invention provides an apparatus for reconstruction of computed tomography (CT) scanning data of an object, comprising a source for generating a projection beam for scanning the object; a rotary unit for mounting and rotating the object relative to the beam; a detector for detecting the beam, the detector receiving CT scanning data of at least one slice of a scanned object; a processor for processing and identifying specific object scanning start orientation data, reconstructing the CT scanning data into reconstructed data in accordance with the identified object scanning start orientation data, identified projection angle and the identified orientation, the reconstructed data capable to be rendered to create a visual expression representative of the object having a predetermined orientation regardless of the starting position of the CT scanning position.

BRIEF DESCRIPTION OF THE DRAWINGS

The present invention is illustrated by way of example of preferred embodiments, and not by way limitation, in the figures of the accompanying illustrative drawings and in which like references numerals refer to similar elements and in which.

DETAILED DESCRIPTION

Figure 2:
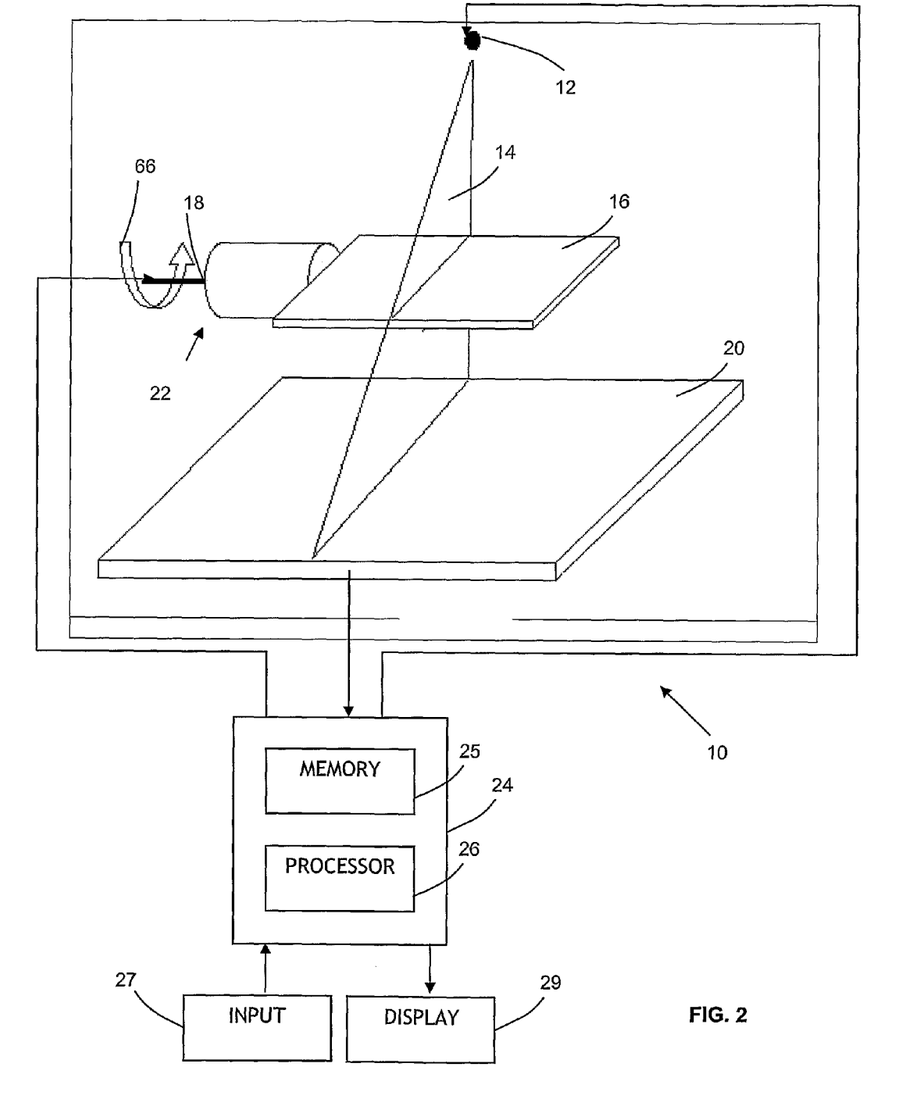
FIG. 2 is a schematic drawing of a system in accordance with an embodiment of the invention.

A system and method in reconstruction of micro CT scanning data is disclosed. In the following description, for the purposes of explanation, numerous specific details are set forth in order to provide a thorough understanding of the present invention. It is apparent to one skilled in the art, however, that the present invention may be practiced without these specific details or with equivalent arrangements. In some instances, well-known structures and devices are shown in block diagram form in order to avoid unnecessarily obscuring the present invention. Referring to FIG. 2, a CT system in accordance with an embodiment of the invention is shown. FIG. 2 illustrates the general concept of a CT system which comprises of a source 12, a direct digital detector (DDD) detector 20, a rotary unit 22 and an examination subject 16, for example an integrated circuit (IC) chip.

The source 12 of the CT system may generate a perspective projection beam 14 or fan-beam projections, parallel beam or perspective projection beam, or the like. The rotary unit may rotate the subject, in at least the direction of rotation 66 indicated, around a rotation axis 18 to generate multiple projections for various angles which then are used for CT reconstruction. The CT system 10 is controlled by the processing system 24 which includes processor 26 responsive to input commands direct from input by a user and/or stored in memory 25 to process data received from detector 20 or input 27 to control rotator 22 of the rotary unit, source 12, and to render a desired output of the data such as a CT image on display 29.

Figures 3A, 3B:
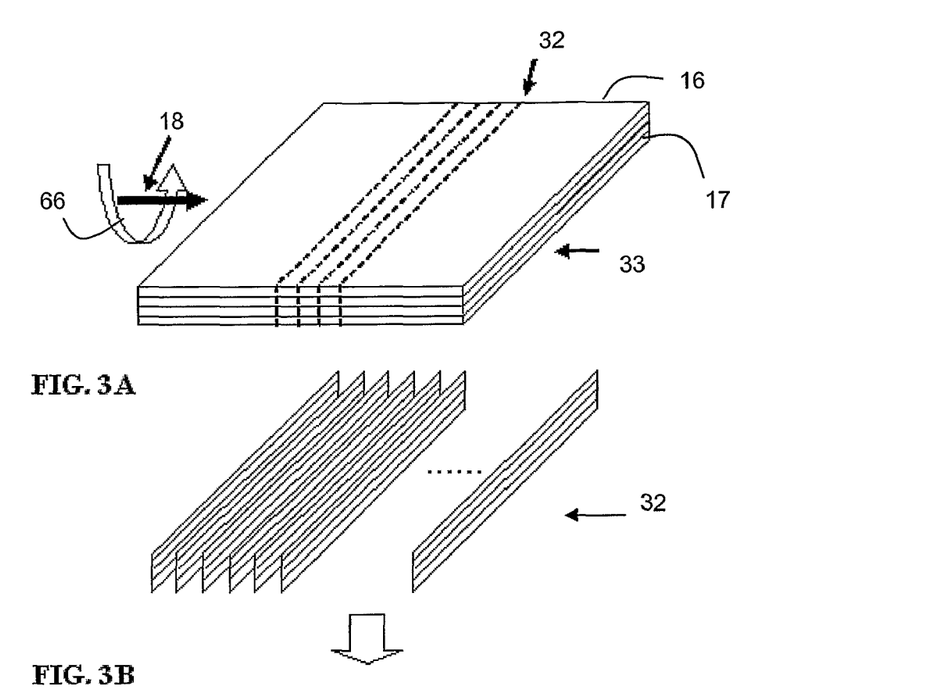
FIG. 3A-D shows a process for multilayered planar object CT and layer separation in accordance with an embodiment of the invention.
Figure 3C:
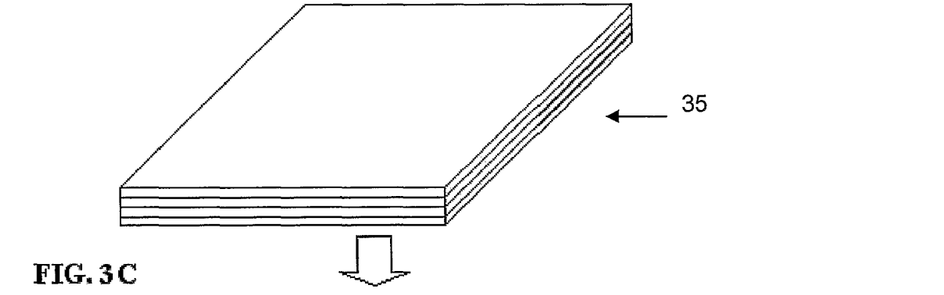
Figure 3D:
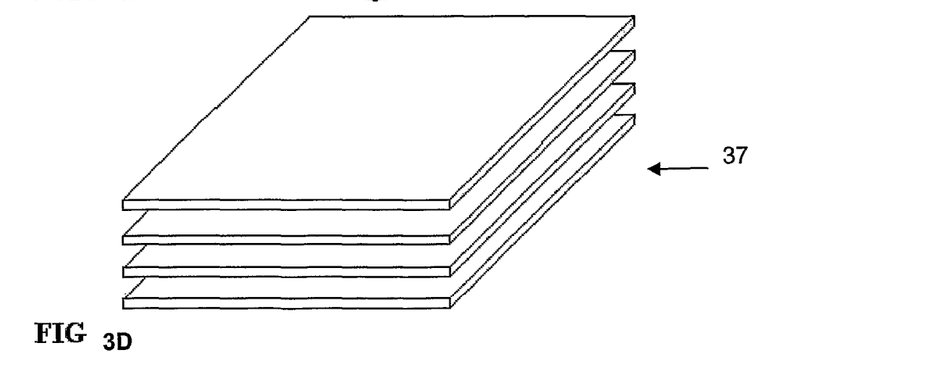

Using the scanned data of the object a sinogram of one cross-section of the object 20 is created. The object is mounted on the rotary unit 22 with its primary plane parallel to the rotation axis 18. In this embodiment, the position data of the sinogram undergoes several transformations for further processing. The fan-beam or perspective projections are converted to non-uniform parallel-beam or perspective projections, and then to uniform parallel-beam projections with a known central ray. The central ray may be determined either by scanning a wire phantom or directly extracting the boundary data of the projections of the object being scanned. FIG. 3A-D shows a process for multilayered planar object CT and layer separation in accordance with an embodiment of the invention. The planar object 16 is mounted with the primary plane 17 of the planar object parallel to the rotation axis 18 of the rotary unit 22. After CT scanning of the multilayered planar sample 33, a certain number of slices 32 are then reconstructed, as shown in FIG. 3B. These slices are then combined to form a volume representation of the object 35, as shown in FIG. 3C, with which the layers are then separated and interpreted 37, as shown in FIG. 3D.

Figure 4:
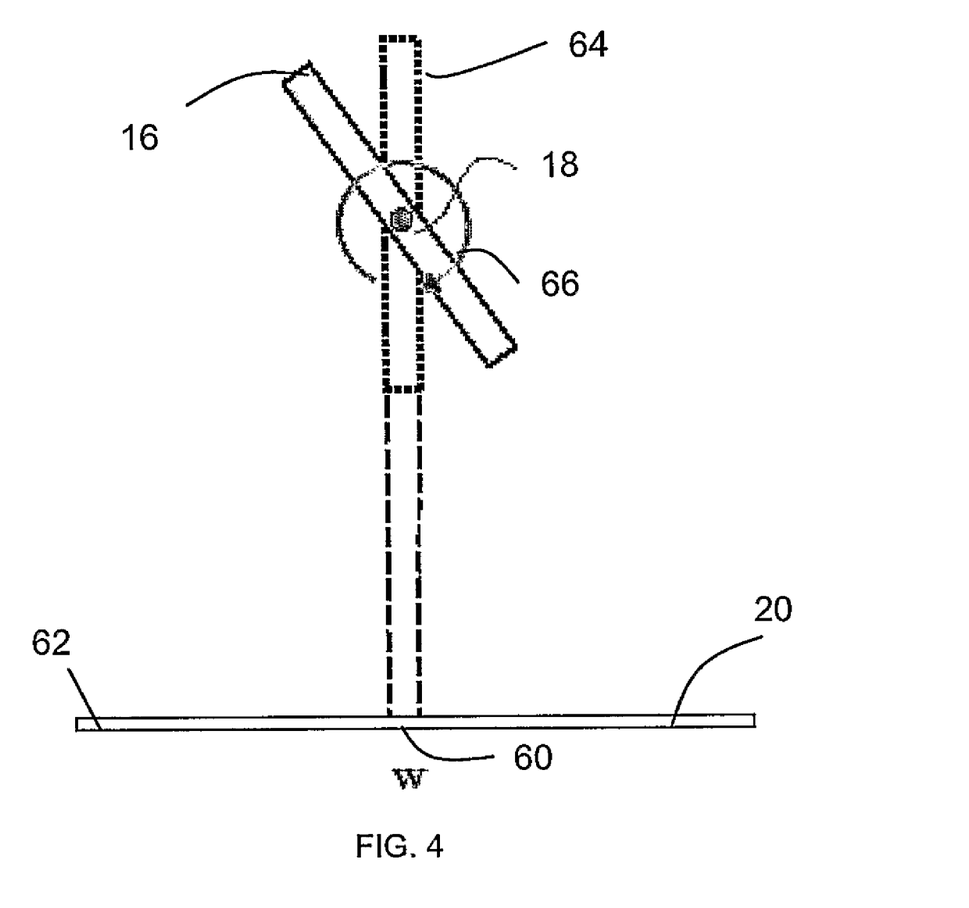
FIG. 4 is a schematic drawing of a sample having an object orientation in the system of FIG. 2 in accordance with an embodiment of the invention.

FIG. 4 describes an embodiment of the invention where the projection of the object will reach the narrowest if the object 20 is planar and has a perpendicular orientation to the detector plane 62 in the course of the scanning as indicated in outline of sample in perpendicular orientation 64. The narrowest width 60 in the sinogram is identified, to the position of the object 20 perpendicular to the detector plane 62 regardless of the initial scanning start orientation of the project. With the uniform parallel-beam projections obtained, the left and right boundary profiles may be extracted. The subtraction of the right boundary vector from the left boundary vector represents the relationship between the projection width of the object and the object scanning step number. The narrowest width is then identified as the smallest value in the projection width vector. The narrowest position then indicates the scanning position of the object that is perpendicular to the detector with this parallel-beam arrangement. For example, if the detector plane 62 is defined as 0°, the identified narrowest position would correspond to an angle of 90°, and if the reconstruction process from the identified angle of 0°, the reconstructed cross-section image of the object would be orientated parallel to the detector plane 62. On the other hand, if the reconstruction starts from the identified angle of 90°, the reconstructed CT image will be perpendicular to the detector plane 62. This embodiment of the invention is a method and/or algorithm that may automatically determine the object orientation with the sinogram of the scanning, which the reconstruction may be performed with the identified scanning start angle position, giving the preferred orientation to the reconstructed images; or the reconstruction may be performed with any other start angle which is intentionally added with a certain offset to the identified scanning start angle, giving other preferred orientation to the reconstructed images.

It will be appreciated that other widths may be used other than the narrowest width. For example, the widest width or another width of the projection width vector may also be used for this purpose. However, for widths other than the narrowest width an error may be introduced due to the increase in width and of object thickness. For example, for the widest width, since the widest projection width actually represents the diagonal length of the rectangular cross section, an error may be introduced and the error increases with the increase of the object thickness.

Figure 5:
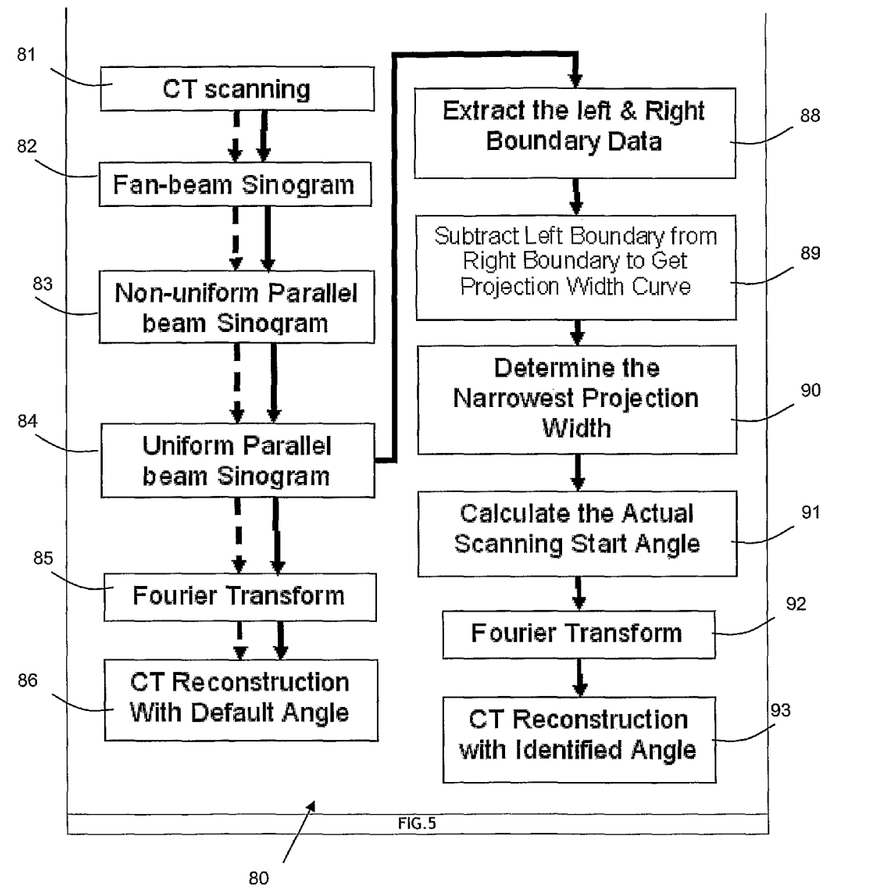
FIG. 5 is a flow chart of a CT reconstruction method in accordance with an embodiment of the invention.

FIG. 5 is a flowchart 80 of the image processing of an embodiment of the invention discussed above. For exemplary purpose, here we only show the fan-beam based reconstruction process, however, this invention should also be applied to cone-beam based reconstruction by any CT expertise. The dashed arrows shown represent the general steps for traditional conventional CT reconstruction, which typically includes acquiring the multiple images 81, then transfer to fan-beam sinogram of slices 82, which is then converted to non-uniform parallel-beam sinogram 83, and then uniform parallel-beam sinogram 84, Fourier transform is then performed 85 for CT reconstruction with default angle 86 that is usually a default start angle. The details of these steps may be found in computed tomography books such as for example Computed Tomography, H. Jiang, SPIE Press 2003; *Principle of Computed Tomographic Imaging*, A. C. Kak and M. Slaney, IEEE Press, 1999; and *Micro-Computed Tomography for Industrial Applications*, Liu Tong, SIMTech Technical Report, 2005. In an embodiment of the invention, essentially, multiple images 81 are acquired, then transfer to fan-beam sinogram of slices 82, which is then converted to non-uniform parallel-beam sinogram 83, and then uniform parallel-beam sinogram 84. Upon obtaining the uniform parallel beam sinogram 84, the boundary data is extracted. In this embodiment, the left and right boundaries of the sinogram may be detected 89 using edge detection algorithms and the subtraction 89 of the right boundary from the left boundary will establish the relationship between the projection width 60 of the object and the projection angle. By identifying the narrowest projection width 90, the angle corresponding to the scanning position perpendicular to the detector plane may be calculated and determined 91, to define the Fourier transform and reconstruction matrix 92, with which the reconstruction 93 may start. It will be appreciated however that with a certain error tolerance, the left and right boundaries may be extracted from the fan-beam scanning data or the non-uniform parallel beam data.

Figure 6A:
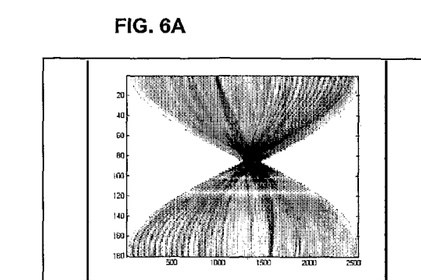
FIG. 6A-D show graphical representations of different steps of an embodiment of the invention which uses the fan-beam data to determine the orientation in accordance with an embodiment of the invention.
Figure 6B:
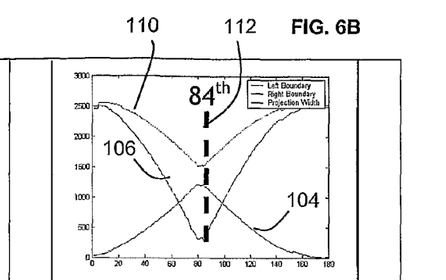
Figure 6C:
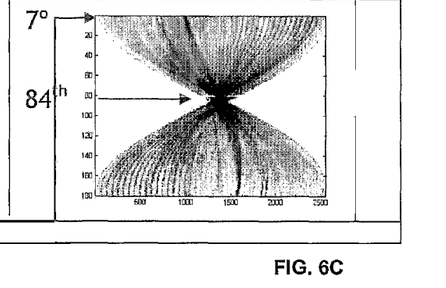
Figure 6D:
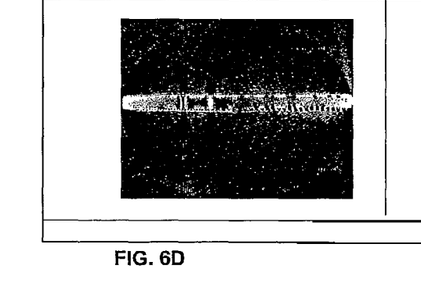

FIG. 6A-D demonstrate a graphical representation of different steps of determining the angle from the obtained parallel-beam sinogram, shown in FIG. 6A, in accordance with an embodiment of the invention. After the narrowest projection width 60 and its corresponding projection angle are obtained, the actual orientation of the object from which the scanning starts (i.e., the real scanning start angle of the object, or the angle for the first image) may be calculated based on the scanning interval (angular step) and the identified sequential number of the image with the narrowest projection width. For example, if the 84$^{th}$ image is found having the narrowest projection width in FIG. 6B where curves of right boundary 110, left boundary 104, and subtracted right-left boundaries 106 shows 84$^{th}$ image 112 in this example as having the narrowest projection. This may be represented, where for example a 1-degree/per step is used, the scanning start angle (the angle for the first image) is then calculated as [90°−(1°/step)*84step+1 degree=7 degree]. The 7° angle is shown in FIG. 6C on the first row of the sinogram in this example. Then the reconstruction shown in FIG. 6D may be conducted with a start angle of 7° instead of a default angle. An alternative way to achieve the purpose is to rotate the sinogram so that identified projection with the narrowest projection will be shifted to the 90$^{th}$ place in the sinogram and the 0° projection may be placed at the first row (the reconstruction start projection).

Figure 7A:
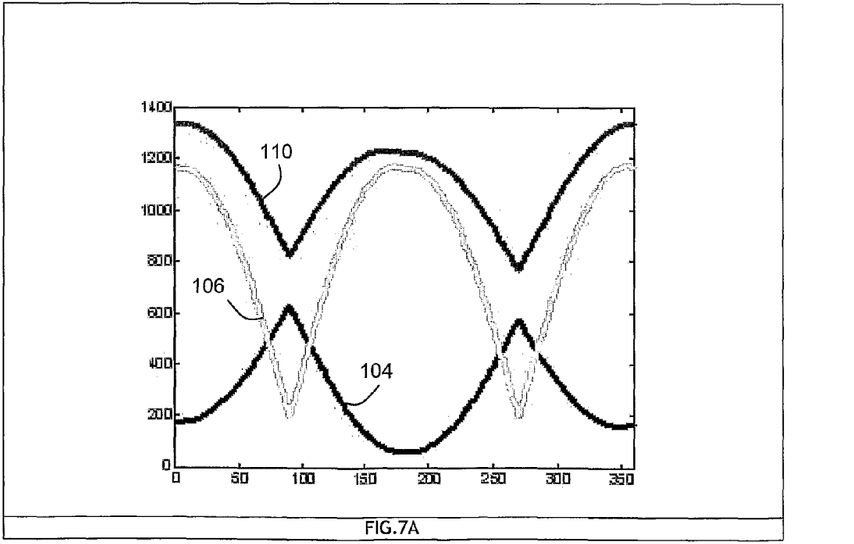
FIG. 7A-B show another embodiment of the invention which applies curve fitting method on one identified projection position to determine a preferred orientation in accordance with an embodiment of the invention.
Figure 7B:
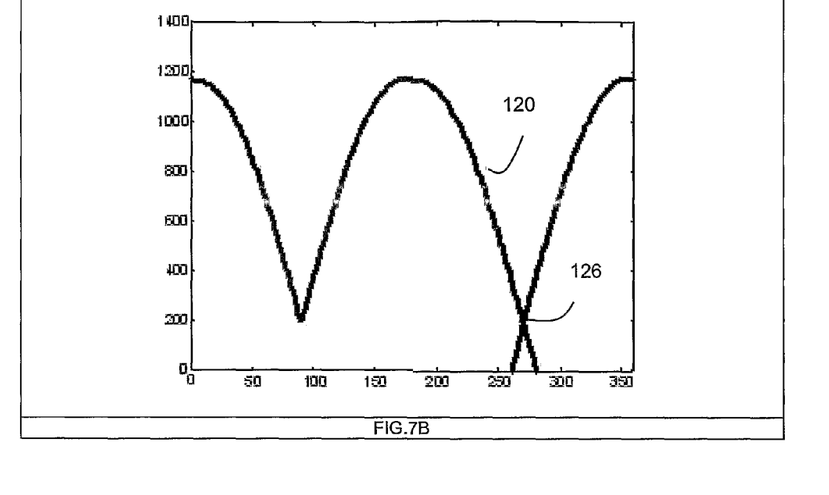

FIG. 7A-B show another embodiment to determine the narrowest width of the projection sinogram for the sake of better accuracy. The minimum point of the projection width curve 120 is identified first. Then curve fitting is applied to the width data to both sides of the identified minimum point. The final narrowest projection position is calculated as the cross point 126 of the two fitted curves.

Figure 8A:
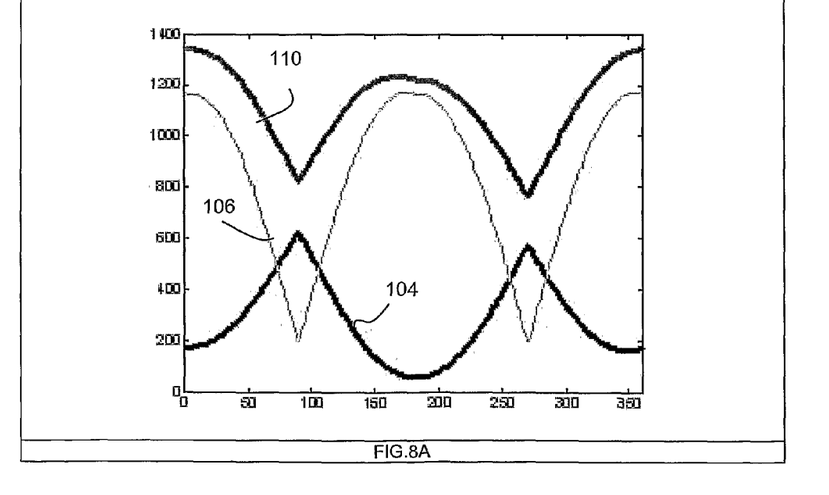
FIG. 8A-B show another embodiment of the invention which applies curve fitting method on two identified 180-degree-apart projection positions to determine a preferred orientation in accordance with an embodiment of the invention.
Figure 8B:
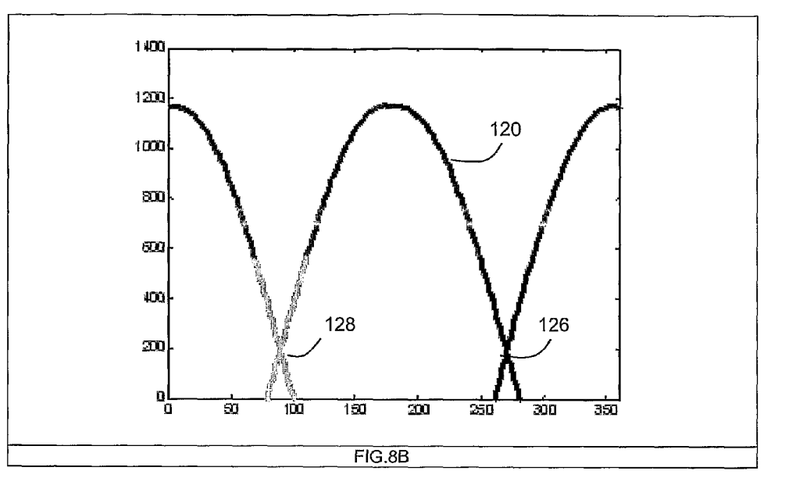

FIG. 8A-B demonstrate another embodiment to determine the narrowest width for the sake of better accuracy. The minimum point of the width curve is identified first. Then curve fitting is applied on the data to both sides of this point, and those data to both sides of another minimum point 128 in a range centered at a point 180° apart from the first minimum point identified. The final narrowest projection position is calculated with results obtained for the two points 126,128.

Figure 9A:
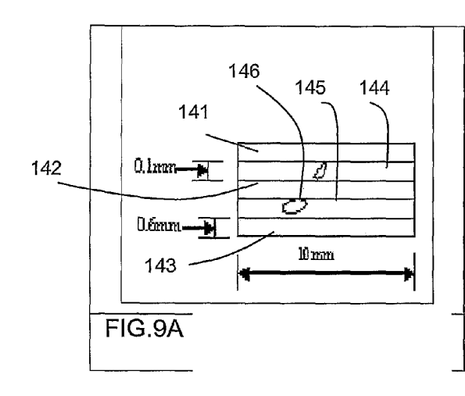
FIG. 9A-E shows several internal layers of a double-layered sandwich chip packaging by a reconstruction method in accordance with an embodiment of the invention.
Figure 9B:
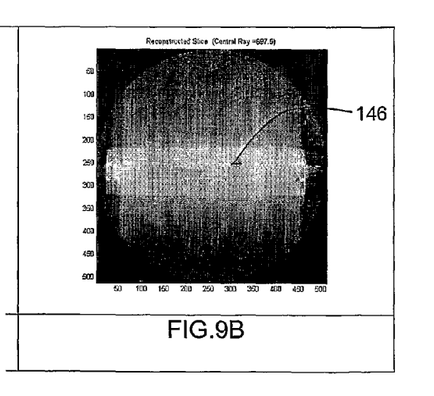
Figure 9C:
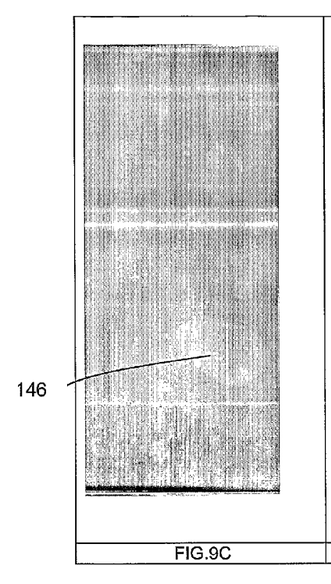
Figures 9D, 9E:
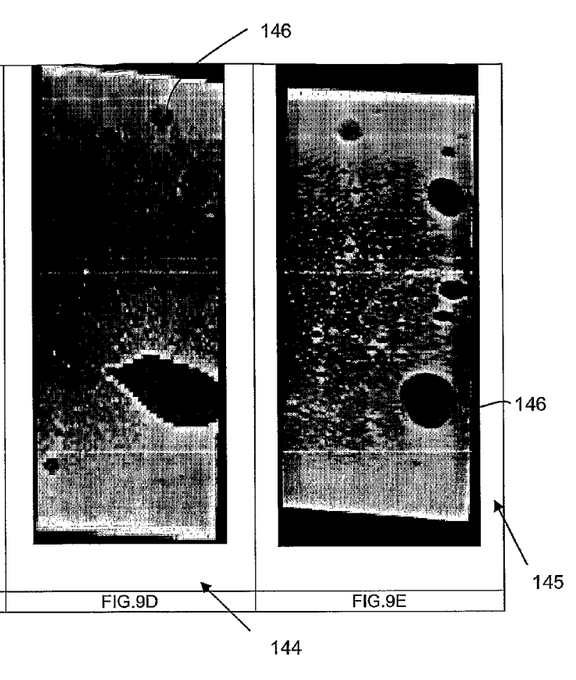

FIG. 9A-E demonstrate the separation of internal layers in a five-layered sandwich packaging with the reconstructed images obtained with preferred orientations. FIG. 9A is a schematic diagram of the sample 16 having a five-layer sandwich chip packaging with a five-layer total thickness of 2 mm. The sample in this example has three silicon layers 141, 142, 143 and two adhesive layers 144,145. FIG. 9B shows one reconstructed slice from which some voids 146 may be seen. FIG. 9C is a 2-dimensional image of the sample of FIGS. 9A and B, and shows the number of voids 146 in the sample, and is used to verify the locations of the voids identified in the CT images. FIGS. 9C, 9D and E show the voids 146 in the adhesive layers 144,145 separately, respectively. In this manner, the locations of the voids may be clearly identified. As shown in FIG. 9B, because the orientation of the reconstructed image is now aligned with the dimensions of the reconstruction matrix, the separation is just as simple and straightforward as to display the layers along one dimension of the reconstruction matrix.

Figure 10A:
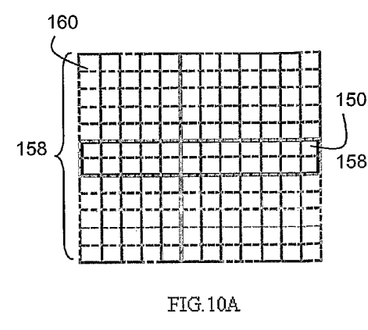
FIG. 10A-C show another aspect of the invention which performs a differential reconstruction for two dimensions of the image in accordance with an embodiment of the invention.
Figure 10B:
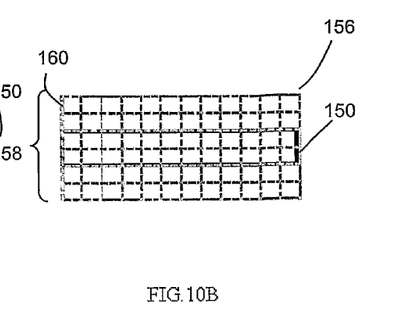
Figure 10C:
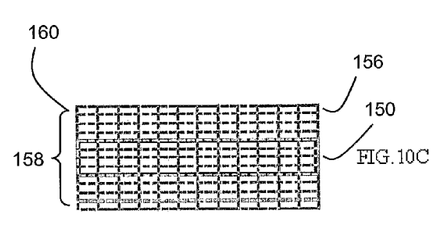

FIG. 10A-C describe another aspect of the invention. In general reconstruction, the reconstruction matrix is an n×n square matrix 152 as shown in FIG. 10A with equal divisions on both dimensions. In an embodiment of the invention, an object 150 may be reconstructed with an object area that may just compass the planar object. With this configuration, a choice may be made of either a) retaining the matrix size, which leads to a higher reconstruction resolution in thickness dimension, or b) maintaining a certain resolution but a smaller matrix size, which leads to a greatly shortened reconstruction time. For example, FIG. 10A is a reconstruction matrix for general object 150 reconstruction (n×n) 152. The size and pitch for both x and y dimensions are equal. In the reconstruction matrix for a flat object (m×n) 154 as shown in FIG. 10B, the size and thickness dimensions 158 is less than that in another dimension and reconstruction time is shortened without degrade to the resolution of the reconstruction. Reconstruction matrix for a flat object (n×n) 156 shown in FIG. 10C, the pitch 160 in the thickness dimension is denser in order to achieve a higher reconstruction resolution in the thickness dimension without increasing the reconstruction processing time.

Figure 11A:
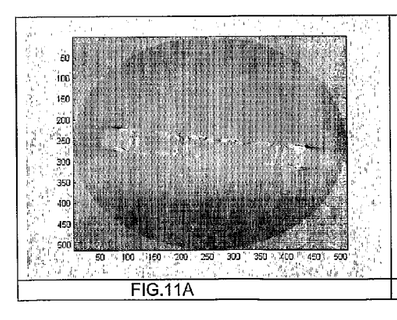
FIG. 11A-D show a demonstration of the aspect of the invention.
Figure 11B:
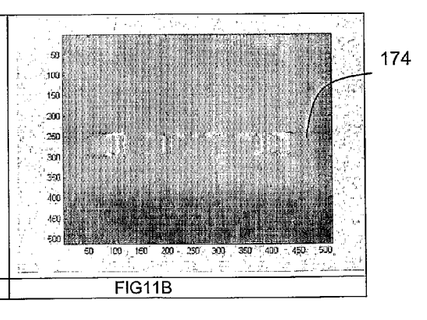
Figure 11C:
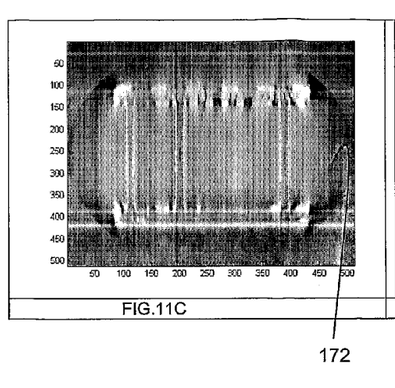
Figure 11D:
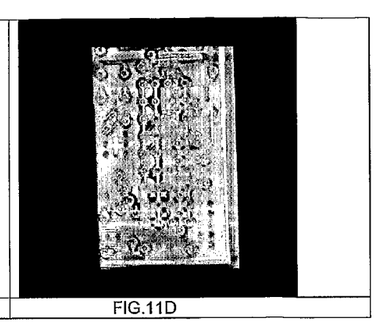

FIG. 11A-D is a demonstration of the aspect of the invention shown in FIG. 10. Traditional CT reconstruction uses an (n-×-n) matrix for reconstruction, as shown in FIG. 11A. The reason for this requirement in conventional CT reconstruction is that the final orientation of the reconstructed object is unknown. In an embodiment of the invention, the same matrix may be applied on an area 174 in FIG. 11B that just covers the planar object, and results in a higher reconstruction resolution 172 in the object thickness dimension than previously achievable with the general reconstruction, as shown in FIG. 11C. FIG. 11D shows a 3-dimensional visualization of the object after performing a multiple slices reconstruction.

Figure 12A:
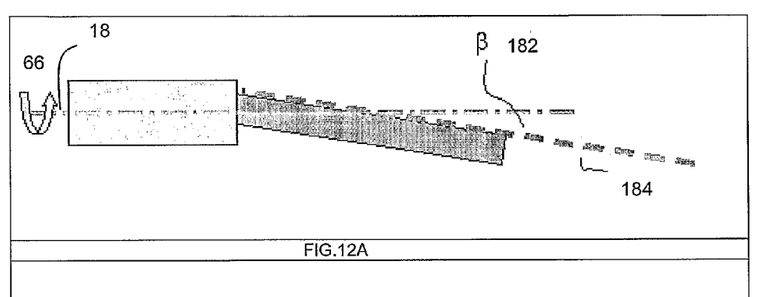
FIG. 12A-B show another aspect of the invention which uses the projection obtained at the identified angle to determine a possible titling angle with respect to the rotation axis in accordance with an embodiment of the invention.
Figure 12B:
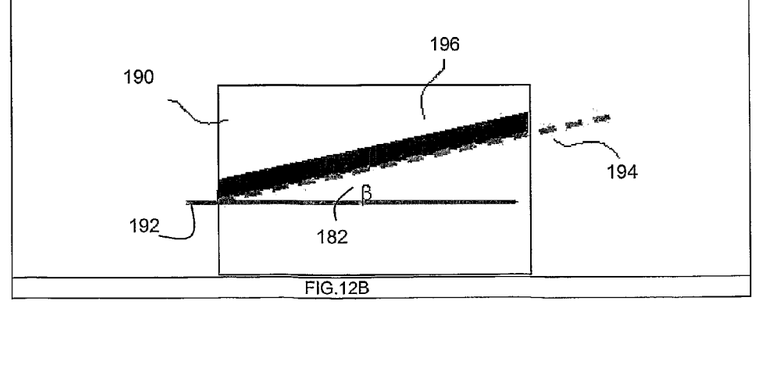

FIG. 12A-B shows another aspect of the invention. If the planar object or a planar internal part of the object is placed at an angle β with respect to the rotation axis 18. After a volume reconstruction (multiple slices reconstruction) is conducted with a preferred orientation using an embodiment of the present invention, for example, another new digital cross sectional image may be generated in another dimension, from which the tilting angle 182 with respect to the rotation axis may be determined by any of the various available boundary/edge detection technologies, which then can be used to perform a digital rotation after a volume reconstruction (multiple slices reconstruction) or cone beam reconstruction, as described in the book *Computed Tomography* mentioned above. FIG. 12A illustrates the situation under which a planar object is mounted with a tilted angle 182 with respect to the rotation axis 18, the tilted angle β may be calculated using the object projection plane 184 shown in FIG. 12B, at the identified angle through any of the various common boundary/edge detection algorithms. The image matrix 190 is shown in FIG. 12B and the object cross-sectional image 196 perpendicular to the rotation axis is shown. The object is now reconstructed with a preferred orientation, the tilting angle 182 may be measured as the angle between the detector plane 192 (one reconstructed image dimension) and the reconstructed object plane 194 that is perpendicular to the rotation axis.

Both the original projections and the parallel-beam projections (after fan-beam to parallel-beam transform) may be used in this embodiment of the invention for the start scanning angle determination. The former may just provide an approximate estimate of the real angle because the above description and mathematical expression are worked out and accurate with parallel-beam projections. However, by establishing some mathematical model and making use of the geometrical relationship between fan-beam and parallel-beam projections, it may also be possible for expertise to accurately determine the start scanning angle using embodiments of the present invention.

Thus, an embodiment of the invention identifies a unique feature of the projection pattern of a planar object to automatically determine the object orientations regardless of the initial scanning orientation of the object so that one object can be always reconstructed with a preferred prescribed orientation. An embodiment of the invention may also include using the boundary data of the parallel-beam sinogram (after fan-beam to parallel-beam conversion) to determine the narrowest width (or the widest width) which corresponds to the orientation of the object cross-section perpendicular (or parallel) to the detector plane. Furthermore, an embodiment of the invention may include the method to rearrange the sinogram so that, the 0-degree projection data of the sinogram is placed at the $1^{st}$ row in the sinogram and becomes the reconstruction start angle, which leads to the reconstructed image aligned with the dimensions of the reconstruction matrix. An embodiment of the invention may include the modification, based on the automatically determined orientation, to the reconstruction algorithm such that the reconstructed slices of the object have a preferred orientation. In general, the preferred orientation is such that the object boundaries within the reconstructed slices are aligned with the dimensions of the reconstruction matrix. However, any preferred orientation can be accommodated.

It is to be understood that the embodiments, as described with respect to FIGS. 2-12B, are for exemplary purposes, as many variations of the specific hardware used to implement the disclosed exemplary embodiments are possible. For example, the functionality of the devices and the subsystems of the embodiments may be implemented via one or more programmed computer system or devices. To implement such variations as well as other variations, a single computer system may be programmed to perform the functions of one or more of the devices and subsystems of the exemplary systems. On the other hand, two or more programmed computer systems or devices may be substituted for any one of the devices and subsystems of the exemplary systems. Accordingly, principles and advantages of distributed processing, such as redundancy, replication, and the like, also may be implemented, as desired, for example, to increase robustness and performance of the exemplary systems described with respect to FIGS. 2-12B.

The exemplary systems described with respect to FIGS. 2-12B may be used to store information relating to various processes described herein. This information may be stored in one or more memories, such as hard disk, optical disk, magneto-optical disk, RAM, and the like, of the devices and sub-systems of the embodiments. One or more databases of the devices and subsystems may store the information used to implement the exemplary embodiments. The databases may be organized using data structures, such as records, tables, arrays, fields, graphs, trees, lists, and the like, included in one or more memories, such as the memories listed above.

All or a portion of the exemplary systems described with respect to FIGS. 2-12B may be conveniently implemented using one or more general-purpose computer systems, microprocessors, digital signal processors, micro-controllers, and the like, programmed according to the teachings of the disclosed exemplary embodiments. Appropriate software may be readily prepared by programmers of ordinary skill based on the teachings of the disclosed exemplary embodiments. In addition, the exemplary systems may be implemented by the preparation of application-specific integrated circuits or by interconnecting an appropriate network of component circuits.

Whilst there has been described in the foregoing description preferred embodiments of the present invention, it will be understood by those skilled in the technology concerned that many variations or modifications in details of design or construction may be made without departing from the present invention.

The invention claimed is:

1. A method for reconstruction of computed tomography (CT) scanning data of an object, comprising:
   scanning the object to create the CT scanning data, wherein the scanning is performed with a CT scanning position that includes a starting position, and the CT scanning data includes a slice of the object
   identifying a projection width representative of a physical feature of the object in the slice of the CT scanning data;
   corresponding the projection width with a projection angle associated with the projection width to determine a scanning start orientation of the object;
   reconstructing the CT scanning data into reconstructed data in accordance with the scanning start orientation; and
   using the reconstructed data to create a visual expression representative of the object having a predetermined orientation regardless of the starting position of the CT scanning position.

2. A method of claim 1, wherein the object is a planar object.

3. A method of claim 1, wherein the object includes an internal planar structure.

4. A method of claim 1, wherein the object is a planar multi-layered object.

5. A method of claim 1, wherein the object is a multi-layered object with all layers being parallel to one another.

6. A method of claim 1, wherein the projection angle is formed by a CT scan beam between a source, the object, and a detector plane of a detector of a CT scan system used to generate the CT scanning data.

7. A method of claim 6, wherein the predetermined orientation is either parallel or perpendicular to the detector plane and an orientation of the object in the reconstructed data is aligned with the predetermined orientation.

8. A method of claim 7, wherein a narrowest projection of the projection width is perpendicular to the detector plane.

9. A method of claim 8, wherein the narrowest projection of the projection width is determined by identifying a first boundary data set and a second boundary data set within a sinogram of the CT scanning data, and subtracting the first boundary data set from the second boundary data set to determine the projection width and the projection angle.

10. A method of claim 9, wherein a projection width curve for the projection width has a projection width curve point that is a minimum projection width curve point or a maximum projection width curve point, and the projection width curve point represents a position of the object.

11. A method of claim 10, further comprising curve fitting both sides of the projection width curve point with projection width data for calculating a first angle.

12. A method of claim 11, further comprising curve fitting both sides of another point 180-degrees apart from the projection width curve point with projection width data for calculating a second angle, and calculating an angle value based on the first angle and the second angle to determine a starting angle of the reconstructed data.

13. A method of claim 1, wherein the CT scanning data is received from a CT scanning system comprising a fan-beam source a parallel beam source, or a cone-beam source.

14. A method of claim 1, wherein the CT scanning data is received from a fan-beam CT scanning system, and further comprising converting fan-beam projection data into parallel-beam projection data.

15. A method of claim 1, further comprising reconstructing the CT scanning data with a first reconstruction matrix size or second reconstruction matrix size, the second reconstruction matrix size is determined by an area of the object and the object is a planar object.

16. A method of claim 1, further comprising calculating a tilting angle of the object with respect to a rotation axis of the object.

17. A method of claim 1, wherein the CT scanning data comprises a projection image, a step number and an angular step size.

18. An apparatus for reconstruction of computed tomography (CT) scanning data of an object, comprising:
a source for generating a projection beam for scanning the object, wherein the scanning is performed with a CT scanning position that includes a starting position;
a rotary unit for mounting and rotating the object relative to the beam;
a detector for detecting the beam, the detector receiving the CT scanning data and the CT scanning data including a slice of the object; and
a processor that (i) identifies a projection width representative of a physical feature of the object in the slice of the CT scanning data, (ii) corresponds the projection width with a projection angle associated with the projection width to determine a scanning start orientation of the object, (iii) reconstructs the CT scanning data into reconstructed data in accordance with a scanning start orientation, and (iv) uses the reconstructed data to create a visual expression representative of the object having a predetermined orientation regardless of the starting position of the CT scanning position.

19. An apparatus of claim 18, wherein the object is a planar object.

20. An apparatus of claim 18, wherein the object includes an internal planar structure.

21. An apparatus of claim 18, wherein the object is a planar multi-layered object.

22. An apparatus of claim 18, wherein the object is a multi-layered object with all layers being parallel to one another.

23. An apparatus of claim 18, wherein the projection angle is formed by the beam, and the beam is between the source, the object, and a detector plane.

24. An apparatus of claim 23, wherein the predetermined orientation is either parallel or perpendicular to the detector plane, and an orientation of the object in the reconstructed data is aligned with the predetermined orientation.

25. An apparatus of claim 24, wherein a narrowest projection of the projection width is perpendicular to the detector plane.

26. An apparatus of claim 25 wherein the narrowest projection of the projection width is determined by identifying a first boundary data set and a second boundary data set within a sinogram of the CT scanning data, and subtracting the first boundary data set from the second boundary data set to determine the projection width and the projection angle.

27. An apparatus of claim 26, wherein a projection width curve for the projection width has a projection width curve point that is a minimum projection width curve point or a maximum projection width curve point, and the projection width curve point represents a position of the object.

28. An apparatus of claim 27, wherein the processor applies curve fitting to both sides of the projection width curve point with projection width data for calculating a first angle.

29. An apparatus of claim 28, wherein the processor applies curve fitting to both sides of another point 180-degrees apart from the projection width curve point with projection width data for calculating a second angle, and calculates an angle value based on the first angle and the second angle to determine a starting angle of the reconstructed data.

30. An apparatus of claim 18, wherein the source is a fan-beam source or a parallel beam source.

31. An apparatus of claim 18, wherein the CT scanning data is received from a fan-beam CT scanning system, and the processor converts fan beam projection data into parallel-beam projection data.

32. An apparatus of claim 18, wherein the processor reconstructs the CT scanning data with a first reconstruction matrix size, or second reconstruction matrix size, the second reconstruction matrix size is determined by an area of the object and the object is a planar object.

33. An apparatus of claim 18, wherein the processor calculates a tilting angle of the object with respect to a rotation axis of the object.

34. An apparatus of claim 18, wherein the CT scanning data comprises a projection image, a step number and an angular step size.

* * * * *

UNITED STATES PATENT AND TRADEMARK OFFICE
CERTIFICATE OF CORRECTION

PATENT NO. : 8,126,108 B2
APPLICATION NO. : 12/596661
DATED : February 28, 2012
INVENTOR(S) : Liu et al.

It is certified that error appears in the above-identified patent and that said Letters Patent is hereby corrected as shown below:

At Page 1, Item 54, Line 2, change "RESCONSTRUCTION" to --RECONSTRUCTION--.

At Column 1, Line 2, change "RESCONSTRUCTION" to --RECONSTRUCTION--.

At Column 8, Line 45, change "object" to --object;--.

At Column 10, Line 24, change "25" to --25,--.

Signed and Sealed this
Third Day of July, 2012

David J. Kappos
*Director of the United States Patent and Trademark Office*